(12) United States Patent
Heo

(10) Patent No.: US 9,131,994 B2
(45) Date of Patent: Sep. 15, 2015

(54) DRILL BIT AND DRILL PROVIDED WITH THE SAME

(71) Applicant: NEOBIOTECH CO., LTD., Seoul (KR)

(72) Inventor: Young Ku Heo, Seoul (KR)

(*) Notice: Subject to any disclaimer, the term of this patent is extended or adjusted under 35 U.S.C. 154(b) by 148 days.

(21) Appl. No.: 13/657,534

(22) Filed: Oct. 22, 2012

(65) Prior Publication Data

US 2013/0046308 A1    Feb. 21, 2013

Related U.S. Application Data

(63) Continuation of application No. PCT/KR2011/002540, filed on Apr. 12, 2011.

(30) Foreign Application Priority Data

Apr. 22, 2010    (KR) .................. 10-2010-0037240

(51) Int. Cl.
*A61B 17/16* (2006.01)
*A61C 8/00* (2006.01)
*A61C 3/02* (2006.01)

(52) U.S. Cl.
CPC ........... *A61C 8/0089* (2013.01); *A61B 17/1615* (2013.01); *A61C 3/02* (2013.01)

(58) Field of Classification Search
CPC ........... A61B 17/1615; B23B 2251/52; B23B 2251/248; B23B 2251/406
USPC ..................... 606/80; 408/202, 207
See application file for complete search history.

(56) References Cited

U.S. PATENT DOCUMENTS 716,441 A * 12/1902 Latham .................. 408/223
4,600,006 A * 7/1986 Baker ..................... 606/173

* cited by examiner

*Primary Examiner* — David Bates
(74) *Attorney, Agent, or Firm* — Park & Associates IP Law, P.C.

(57) ABSTRACT

The present invention discloses a drill bit 100 comprising a plurality of cutting blade portions 131 for gradually cutting the surface and the inner wall of bones, a plurality of channels 132 for temporarily storing bone chips produced to be agglomerated by the cut bones and for discharging outside the chips, and a working portion 130 having a blocking portion for blocking further approach of the drill bit 100 after it approaches in the bones as much as the length of the plurality of cutting blade portions 131, wherein the plurality of cutting blade portions 131 and the plurality of channels 132 are alternatively formed to have equal interval in circumferential direction, and at least portion of the bone chips produced to be agglomerated in the plurality of channels 132 is located before the plurality of cutting blades 131.

18 Claims, 7 Drawing Sheets

DRILL BIT AND DRILL PROVIDED WITH THE SAME

REFERENCE TO RELATED APPLICATIONS

This is a continuation of pending International Patent Application PCT/KR2011/002540 filed on Apr. 12, 2011, which designates the United States and claims priority of Korean Patent Application No. 10-2010-0037240 filed on Apr. 22, 2010, the entire contents of which are incorporated herein by reference.

FIELD OF THE INVENTION

The present invention relates to a drill bit, and more particularly, relates to a drill bit and a drill provided with the same enabling to accurately, precisely and quickly drill bones in a predetermined position without giving damage to other important parts in the bones even if the bone is very thin.

BACKGROUND OF THE INVENTION

The human skeleton consists of plural kinds of so many bones such as upper and lower jawbones, spine or skull, and for example a case to drill the upper and lower jawbones for implant or a case to drill spine or skull for surgery related diseases is frequently occurred.

Many tools such as drills to drill various bones are developed, and a representative example is disclosed in ⌈ENDOSSEOUS IMPLANT DRILL⌋ of U.S. Pat. No. 6,641,395. The representative components are shown in FIGS. 1 and 2.

FIG. 1 is a side view of a conventional implant drill bit, and FIG. 2 is an enlarged view of FIG. 1.

As shown in FIG. 1, an implant drill bit 10 consists of a mounting portion 22 to be mounted a dental hand-piece, a working portion 24 for cutting bones and a collar 26 to connect them.

The working portion 24 includes a plurality of "V" typed longitudinal channels 39. The plurality of "V" typed longitudinal channels 39 defines a plurality of end cutting blades 36 and a plurality of axial cutting edges 34 which are finished at a cutting tip 35 inclusive of a distal-most end 38. The plurality of axial blades 34 is straightly extended almost parallel to a longitudinal axis 11, and they are arranged with equal interval in about 120°. And, the working portion 24 includes a longitudinal fluid passageway 40 from which a fluid is passed through a collar through hole 32.

Each blade 34 has a leading blade surface 34a, a trailing blade surface 34b, a leading side edge 37a and a trailing side edge 37b. On the trailing blade surface 34b of the blades 34, fluid discharge ports 42 are formed adjacent to the end cutting blades 36.

Each end cutting blade 36 has a leading cutting edge 36a and a trailing edge 36b to form a relief surface 122 therebetween, a leading blade surface 124 and a trailing blade surface 120, and also the crossing portion of the leading blade surface 124 and the relief surface 122 will be the leading edge 36a. Furthermore, each end cutting blade 36 includes a leading edge 46a and a trailing edge 46b, or connects to them. The leading blade surfaces 124 have inner edges 72 oriented at an angle θ with respect to the longitudinal axis 11, and the end cutting blades 36 are diverged at an angle β(<90°) with respect to the longitudinal axis 11.

The conventional implant drill bit 10 having the above-explained structure, leading blade surfaces 124 have inner edges 72 oriented at an angle θ with respect to the longitudinal axis 11, and the end cutting blades 36 are diverged at an angle β(<90°) with respect to the longitudinal axis 11, and therefore it can cut a desired amount of bones in short time and then can easily drill holes in a desired depth.

However, the conventional drill bit 10 can be moderately applied to cases in that bone depth is enough deep, bone thickness is enough thick, or fortunately other important parts such as membranes, nerves or cells are not present, but in cases that bone depth is light, bone thickness is thin, or fortunately other important parts such as membranes, nerves or cells are present, even a very skillful person should very carefully do drilling to give no damage to these important parts. Furthermore, in case that the drilling is proceeding in high speed of 2,000~10,000 rpm, by even very skillful person, unwanted problems are often occurred, for example, other important parts such as membranes, nerves or cells are damaged or the membranes are torn, the nerves or cells are died.

SUMMARY OF THE INVENTION

The present invention are invented to solve the above mentioned problems of the conventional art, one object of the present invention is to provide a drill bit and a drill provided with the same enabling to prevent that other important parts are damaged, for example, membranes are torn or nerves or cells are died, by the cut bone chips being constantly remained between the plurality of cutting blades at very before the cutting blades and then the bones chips are rotated to be contacted to the membranes, nerves or cells but the blades are rotated to be not contacted to them, when the drill bit penetrates in bones and meets a portion having a lower density relative to bones such as membranes, nerves or cells.

Another object of the present invention is to provide a drill bit and a drill provided with the same enabling to prevent that other important parts are damaged, for example, membranes are torn or nerves or cells are died, by bones present before cutting blades of the drill bit are broken in a disk type by the proceeding force of the drill bit at near the inside of the bones when the drill bit penetrates in the bones and then the broken disk typed bones are rotated to be contacted to the membranes, nerves or cells but the blades are rotated to be not contacted to them, when the drill bit penetrates in bones and meets a portion having a lower density relative to bones such as membranes, nerves or cells.

To accomplish the objects of the present invention, the present invention provides a drill bit comprising a plurality of cutting blade portions for cutting the surface and the inner wall of bones, a plurality of channels for temporarily storing bone chips and to be agglomerated therein before discharging outside, and a working portion having a blocking portion for blocking further approach of the drill bit after it approaches in the bones as much as the length of the cutting blade portions, wherein the plurality of cutting blade portions and the plurality of channels are formed to have equal interval in circumferential direction, and at least portion of the bone chips produced in the plurality of channels is cumulated before the plurality of cutting blades.

The drill bit of the present invention further comprises a mounting portion provided to be one body with the working portion, for mounting the working portion to a drill.

Further, the plurality of cutting blade portions and the plurality of channels are three, respectively, and they are formed to have equal interval of 120° with respect to the central axis, and the plurality of cutting blade portions meet at one merging point on the central axis.

Herein, the merging point has steeper tilt angle than a tilt angle of the plurality of cutting blade portions, and the plurality of cutting blade portions have end cutting blades, cutting corners and side cutting edges which are extended toward the blocking portion to be integrally connected.

And, the end cutting blades cut the surface of the bones, and they have a tilt angle of 7°~9° with respect to the line perpendicular to the central axis, and the height of the end cutting blades obtained following to the central axis is 0.2 mm~0.5 mm, and the side cutting edges cut the side wall of the bones, and they outwardly have a tilt angle of 7°~9° with respect to the central axis, and the height of the side cutting edges obtained following to the central axis is 1.0 mm~5.0 mm, and the cutting corners are roundly formed to have a radius of curvature of 0.4 mm~0.6 mm, and the height of the cutting corners obtained following to the central axis is 0.2 mm~0.7 mm, and the plurality of channels have a tilt angle corresponding to the tilt angle of the side cutting edges.

Further, a side surface formed with the end cutting blades, the cutting corners and the side cutting edges is formed with trailing cutting blades, trailing cutting corners and trailing side cutting edges on opposite end thereof.

Herein, the side surface outwardly has a tilt angle of 7°~9° with respect to the central axis, and the trailing cutting blades have a tilt angle of 20°~40° with respect to a line perpendicular to the central axis, and the trailing side cutting edges inwardly have a tilt angle of 15°~25° with respect to the central axis, and the plurality of channels consist of main channels having a tilt angle corresponding to the tilt angle of the side cutting edges and subsidiary channels having a tilt angle corresponding to the tilt angle of the trailing side cutting corners, and a surface defined by the end cutting blades and the trailing cutting blades consists of a cutting surface and a relief surface, and the surface is perpendicular to the side surface.

Further, a edge at which the surface and the side surface meet is roundly formed to have a radius of curvature of 0.3 mm~0.5 mm, and the cutting surface is near to the end cutting blades and the relief surface is near to the trailing cutting blades, and the side surface is formed to be curved toward the central axis following to the circumferential direction thereof, and the cutting surface has a tilt angle of 8°~12° with respect to a virtual surface perpendicular to the central axis.

The present invention further provides a drill provided with the drill bit disclosed above.

According to a drill bit and a dill provided with the same, it can be prevented that other important parts are damaged, for example, membranes are torn or nerves or cells are died, because the cutting bone chips are constantly remained between the plurality of cutting blades at very before the cutting blades and then the bones chips are rotated to be contacted to the membranes, nerves or cells but the blades are rotated to be not contacted to them, when the drill bit penetrates in bones and meets a portion having a lower density relative to bones such as membranes, nerves or cells.

Furthermore, it can be prevented that other important parts are damaged, for example, membranes are torn or nerves or cells are died, because bones present before cutting blades of the drill bit are broken in a disk type by the proceeding force of the drill bit at near the inside of the bones when the drill bit penetrates in the bones and then the broken disk typed bones are rotated to be contacted to the membranes, nerves or cells but the blades are rotated to be not contacted to them, when the drill bit penetrates in bones and meets a portion having a lower density relative to bones such as membranes, nerves or cells.

With the effect like those, even an unskillful person, without worry, can easily drill bones other important parts such as membranes, nerves or cells present in the bones and then can finish greatly desired implant surgery.

DETAILED DESCRIPTION OF THE INVENTION

Hereinafter, a drill bit and a drill provided with the same according to a preferred embodiment of the present invention will be explained in detail with reference to the accompanying drawings.

Figure 1:
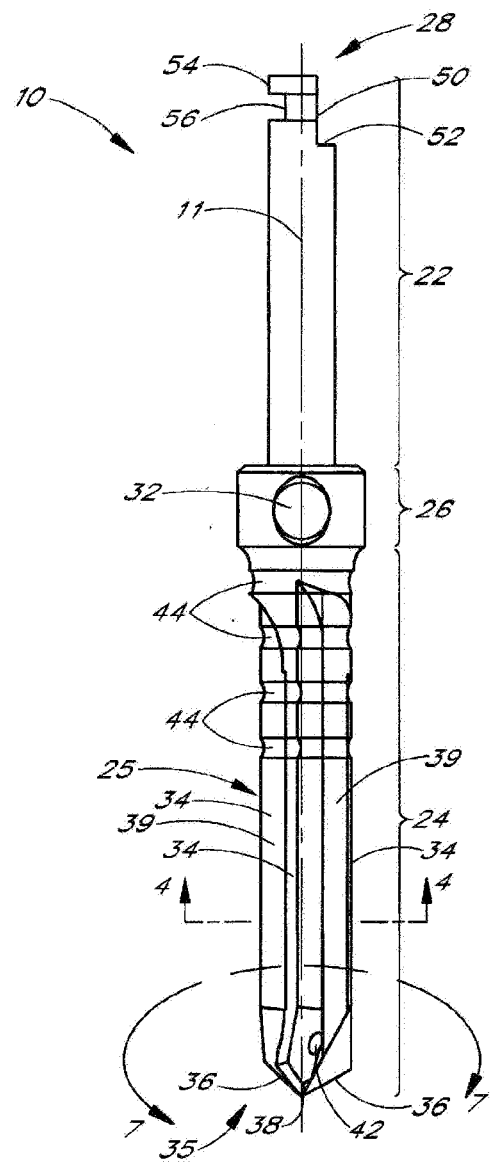
FIG. 1 is a side view of an implant drill bit known in the art.
Figure 2:
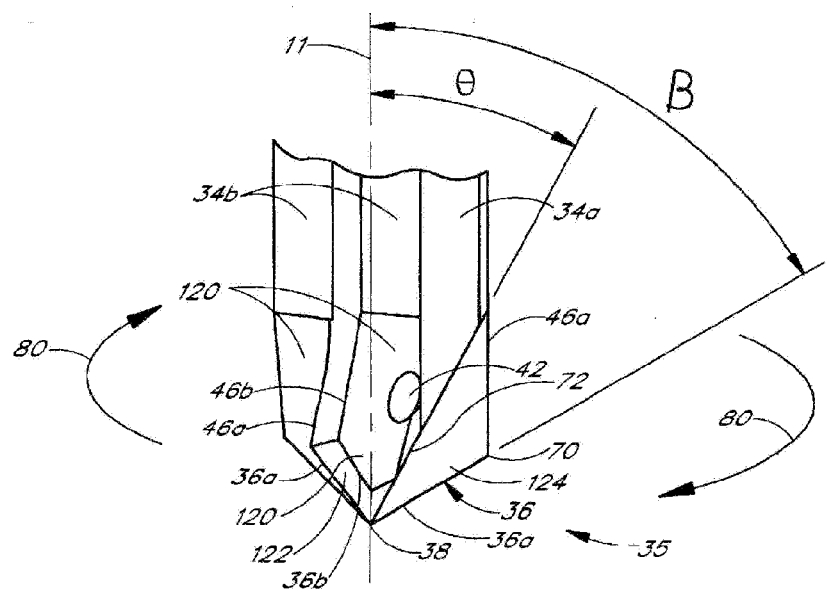
FIG. 2 is an enlarged view of a cutting tip of FIG. 1 known in the art.
Figure 3:
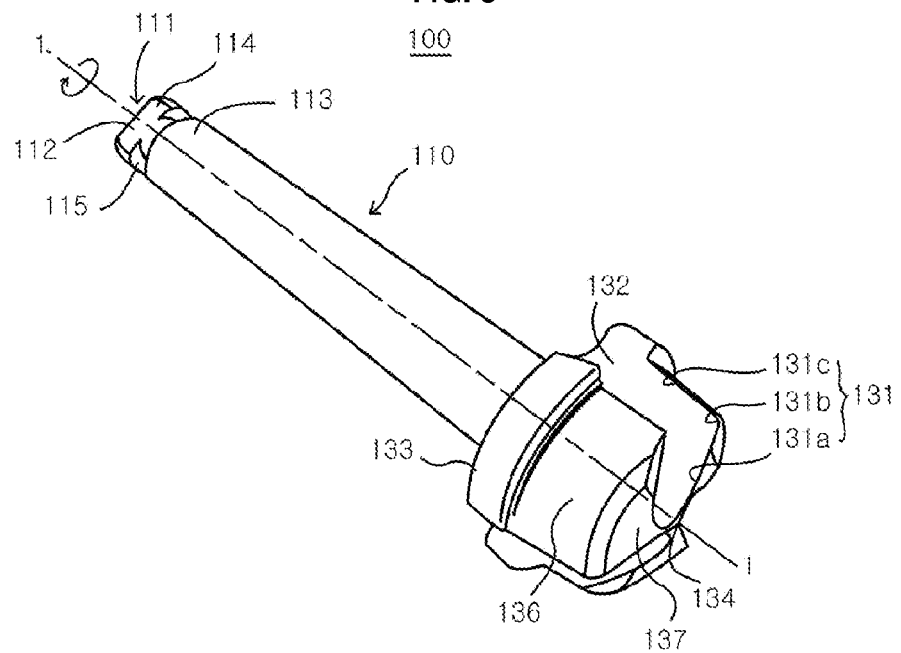
FIG. 3 is a perspective view illustrating a drill bit according to the preferred embodiment of the present invention.
Figure 4:
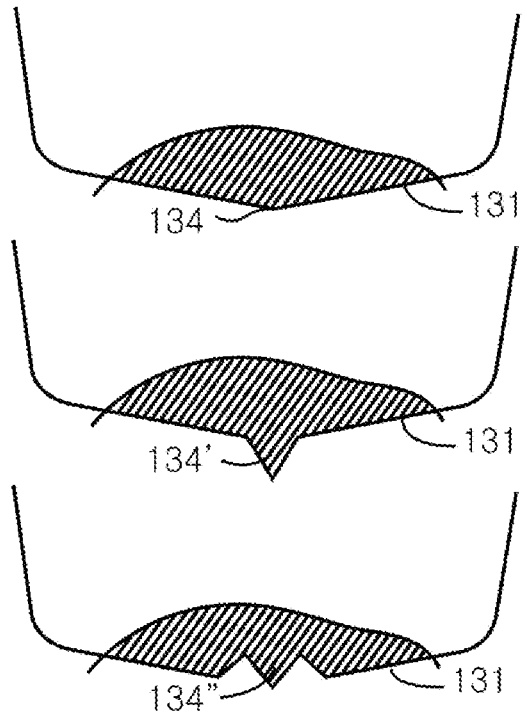
FIG. 4 is a sectional view illustrating various examples of a merging potion of FIG. 3.
Figure 5:
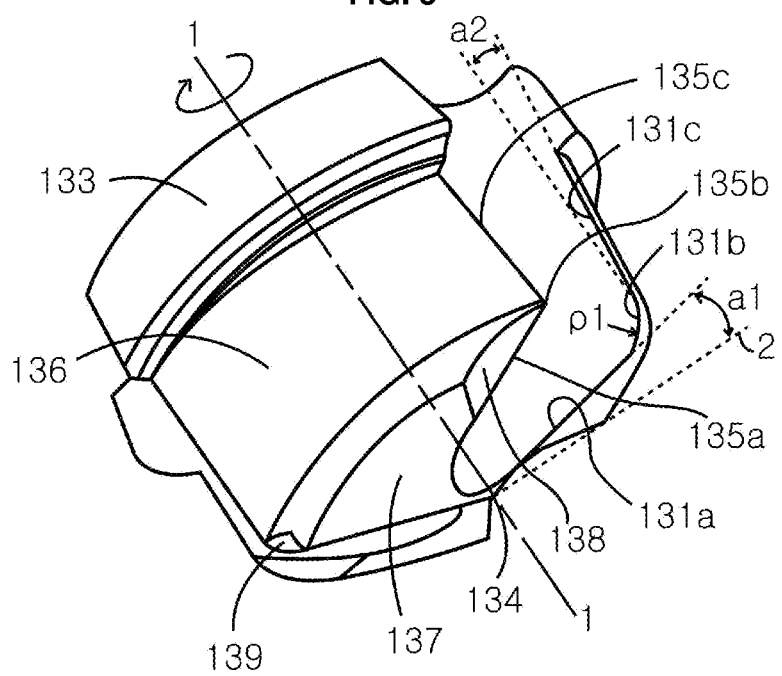
FIG. 5 is an enlarged perspective view illustrating a working portion of the drill bit of FIG. 3.
Figure 6:
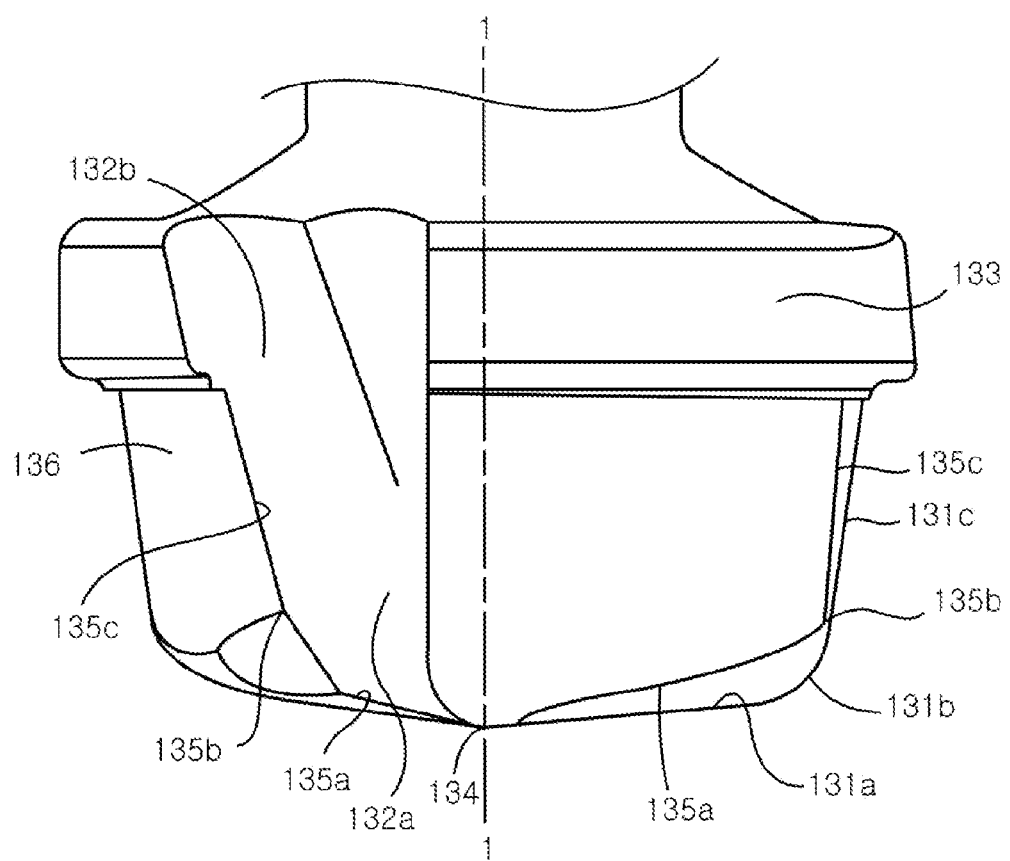
FIG. 6 is a side view showing the drill bit of FIG. 5 in one direction.
Figure 7:
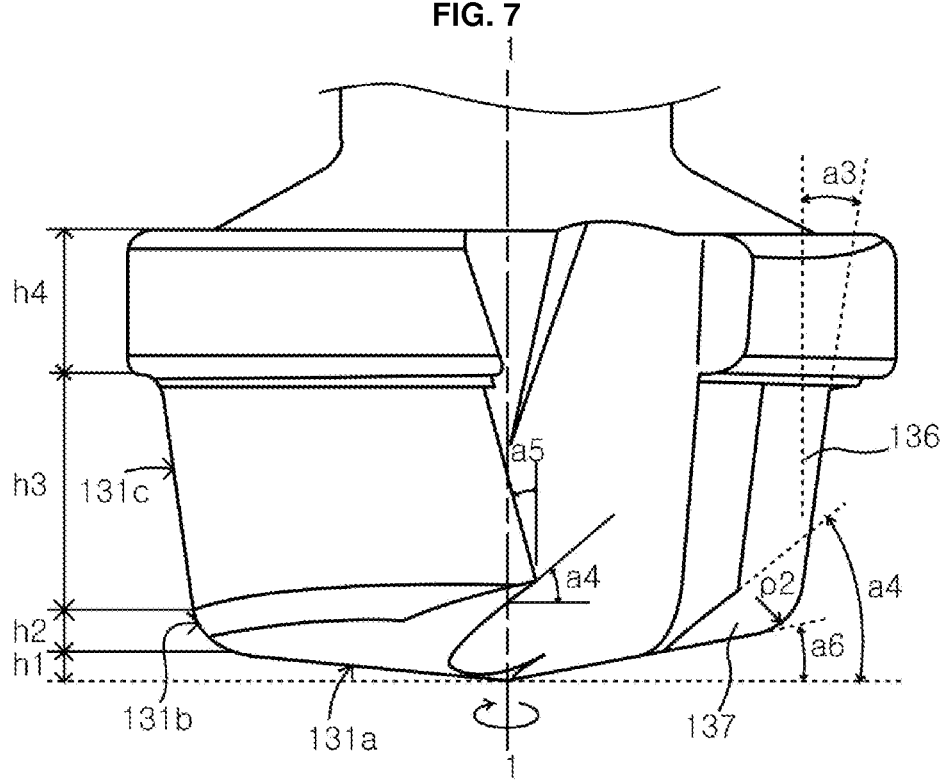
FIG. 7 is a side view showing the drill bit of FIG. 5 in another direction.
Figure 8:
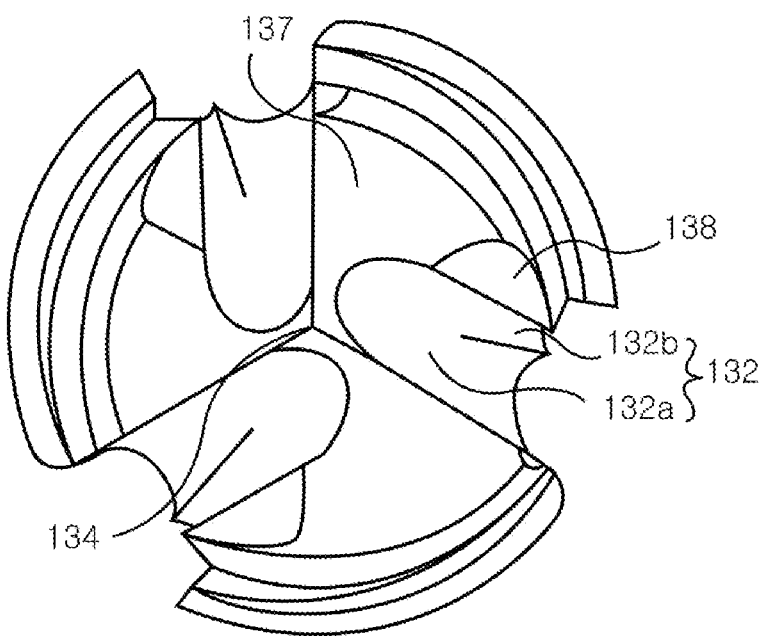
FIG. 8 is a front view of the drill bit of FIG. 5.

FIG. 3 is a perspective view illustrating a drill bit according to the preferred embodiment of the present invention, FIG. 4 is a sectional view illustrating various examples of a merging potion of FIG. 3, FIG. 5 is an enlarged perspective view illustrating a working portion of the drill bit of FIG. 3, FIG. 6 is a side view showing the drill bit of FIG. 5 in one direction, FIG. 7 is a side view showing the drill bit of FIG. 5 in another direction, and FIG. 8 is a front view of the drill bit of FIG. 5.

As shown in FIGS. 3 to 8, a drill bit 100 of the present invention comprises a mounting portion 110 and a working portion 130. The drill bit 100 will be mounted to a drill (or a hand-piece) to be rotated in arrow direction, that is, in clockwise direction preferably with respect to the central axis 1, alternatively, to meet other conditions, it may be mounted to a drill to be rotated in opposite direction, that is, in counter-clockwise direction.

The mounting portion 110 is applied to be mounted to a hand-piece, and it is provided with a chuck 111 having a size and shape to be able to be mounted to a general hand-piece or drill.

The chuck 111 has a substantially "D" shaped cross section, and also has a substantially "I" shaped flat side 112. A semi-circle shaped disk 114 and a semi-circle shaped groove 115 are formed by the "I" shaped flat side 112. The remained mounting portion 110 except for the chuck 111 has a cylindrical shape having same diameter in longitudinal direction.

The working portion 130 is applied to cut or remove bones, and it consists of a plurality of cutting blade portions 131 for gradually cutting the surface and the inner wall of the bones, a plurality of channels 132 for temporarily storing bone chips produced to be agglomerated by the cut bones and discharging outside them, and a blocking portion 133 for blocking further approach of the drill bit 100 after it approaches in the bones as much as the length of the cutting blade portions 131. In this embodiment, three cutting blade portions 131 and three channels 132 are alternatively formed to have equal interval of 120° in circumferential direction. However, differently, a desired number of cutting blade portions 131 and channels 132 may be formed to have a equal interval, for example two cutting blade portions 131 and channels 132 are formed to have a interval of 120°, four cutting blade portions 131 and channels 132 are formed to have a interval of 90°, and five cutting blade portions 131 and channels 132 are formed to have a interval of 72°.

The plurality of cutting blade portions 131 are merged at one merging point 134 on the central axis 1, and end cutting blades 131a, cutting corners 131b and side cutting edges 131c are extended toward the blocking portion 133 to be integrally connected in one body.

The merging point 134 is sharply formed to be one point, and, as shown in section in FIG. 4, it may be formed to have the same tilt angle as the plurality of cutting blade portions 131. However, it may be slightly protruded following to the central axis 1 like reference numeral 134' or may have slightly cut portion on its surroundings like reference numeral 134" following to the central axis 1, to have sharper tilt angle than the cutting blade portions 131. If the merging point is formed in 134' or 134", the drill bit 100 is not run idle on the bone surface when a drilling is begun and then the drilling can be begun and finished on the desired correct position.

The end cutting blades 131a, a main cutting blade portion, cut the surface of the bones, and they are formed to have preferably a tilt angle (a1) of 7°~9°, further preferably a tilt angle (a1) of 8° with respect to the line 2 perpendicular to the central axis 1. If the tilt angle (a1) is smaller than 7°, the bones are so finely cut and then the cut bone chips are not well agglomerated, and if greater than 9°, the bones are so thickly cut and then also the cut bone chips are not well agglomerated. Therefore, any case, it is difficult to be accomplished the object of the present invention in which the cut bone chips are well agglomerated in the channels 132 and then they are constantly remained very before the cutting blades.

The side cutting edges 131c, a subsidiary cutting blade portion, cut the side wall of the bones, and they are formed to outwardly have preferably a tilt angle (a2) of about 7°~9°, further preferably a tilt angle (a2) of 8° with respect to the central axis 1. If the tilt angle (a2) is smaller than 7°, the bones are so finely cut and then the cut bone chips are not well agglomerated, and if greater than 9°, the bones are so thickly cut and then also the cut bone chips are not well agglomerated. Therefore, any case, it is difficult to be accomplished the object of the present invention in which the cut bone chips are well agglomerated in the channels 132 and then they are constantly remained very before the cutting blades.

The cutting corners 131b, blade portions between the end cutting blades 131a and the side cutting edges 131c, and they are roundly formed to have preferably a radius of curvature (ρ1) of 0.4 mm~0.6 mm, further preferably a radius of curvature (ρ1) of 0.5 mm. If the radius of curvature (ρ1) is smaller than 0.4 mm, a corner portion which is not cut by the end cutting blades 131a and the side cutting edges 131c is not well cut and then the drill bit 100 is difficult to be proceeded, and if greater than 0.6 mm, the length of the end cutting blades 131a and/or side cutting edges 131c is shorter and then the surface or the side wall of the bones are difficult to be well cut.

Side surfaces formed with the end cutting blades 131a, the cutting corners 131b and the side cutting edges 131c are also formed with trailing cutting blades 135a, trailing cutting corners 135b and trailing side cutting corners 135c. The end cutting blade 131a, the cutting corner 131b and the side cutting edge 131c formed on one side surface 136 do respectively face with the trailing cutting blade 135a, the trailing cutting corner 135b and the trailing side cutting corner 135c formed on the other side 136, across the channel 132. The side 136 is formed to have a tilt angle (a3) outwardly with respect to the central axis 1 as like the tilt angle (a1).

The trailing cutting blades 135a are formed to have a tilt angle (a4) of about 20°~40°, preferably 35°, which is slightly greater than the tilt angle (a1) of the end cutting blades 131a, with respect to the line 2 perpendicular to the central axis 1, and the trailing side cutting corners 135c are formed to inwardly have a tilt angle (a5) of about 15°~25°, preferably 23°, which is slightly greater than the tilt angle (a2) of the side cutting edges 131c, with respect to the central axis 1. The trailing cutting corners 135b is sharply formed unlike to the rounded cutting corners 131b. With this structure, when the drill bit 100 is rotated to cut the bones in arrow direction, that is the clockwise direction, the end cutting blades 131a cuts the surface of the bones but the trailing cutting blades 135a is not contacted to the cut surface and they are slightly over the cut surface, and the side cutting edges 131c cut the inside wall of the bones but the trailing side cutting corners 135c are not contacted to the inside wall of the bones and they are slightly over the inside wall of the bones.

The surface defined by the end cutting blades 131a and the trailing cutting blades 135a consists of cutting surfaces 137 and relief surfaces 138, and it is substantially perpendicular to the side surface 136. The corner 139 at which this surface and the side surface 136 is roundly formed to have a radius of curvature (ρ2) of 0.3 mm~0.5 mm, further preferably a radius of curvature (ρ2) of 0.4 mm. The cutting surface 137 is near to the end cutting blades 131a and the relief surface 138 is near the trailing cutting blades 135a. The side surface 136 is formed to be further curved toward the central axis following to the circumferential direction. With this structure, the production of the friction heat by the side surface 136 can be greatly decreased when the drill bit 100 is rotated to cut bones.

The cutting surface 137 is preferably formed to have a tilt angle (a6) of about 8°~12°, preferably 10° with respect to the virtual surface perpendicular to the central axis 1. Also, the relief surface 138 has the same tilt angle as the tilt angle (a4) with respect to the virtual surface perpendicular to the central axis 1. Furthermore, the ratio of the area occupied by the cutting surfaces 137 and the area occupied by the relief 138 is 0.8~1.5:1, preferably 1:1. With this structure, the production of the friction heat by the cutting surface 137 can be greatly decreased when the drill bit 100 is rotated to cut bones.

The plurality of channels 132 constantly store the bone chips produced by the cutting of the plurality of cutting blade portions 131 and discharge the bone chips, and they are provided between the plurality of cutting blade portions 131 to begin at the merging point 134 and to be extended to the blocking portion 133.

The channels 132 consist of main channels 132a having a tilt angle corresponding to the tilt angle (a2) of the side cutting edges 131c and subsidiary channels 132b having a tilt angle corresponding to the tilt angle (a5) of the trailing side cutting corners 135c. The subsidiary channels 132b begins at about midpoint of the main channels 132a and it is extended to the blocking portion 133. The size of the particles of the bone chips to be able to be constantly stored in channels 132 in agglomerated condition is preferably about 100 μm~300 μm. In this embodiment, the channels 132 are formed to be divided the main channels 132a and the subsidiary channels 132b, however only main channels 132a may be formed without the subsidiary channels 132b.

The blocking portion 133 blocks further approach of the drill bit 100 after it approaches in bones as much as the length of the plurality of cutting blade portions 131, and it is provided to have slightly greater diameter than the plurality of side surfaces 136.

The height (h1) of the end cutting blades 131a obtained following to the central axis 1 is about 0.2 mm~0.5 mm, the height (h2) of the cutting corners 131b is about 0.2 mm~0.7 mm, the height (h3) of the side cutting edges 131c is about 1.0 mm~5.0 mm, and the height (h4) of the blocking portion 133 is about 0.8 mm~1.3 mm, preferably.

Figure 9A:
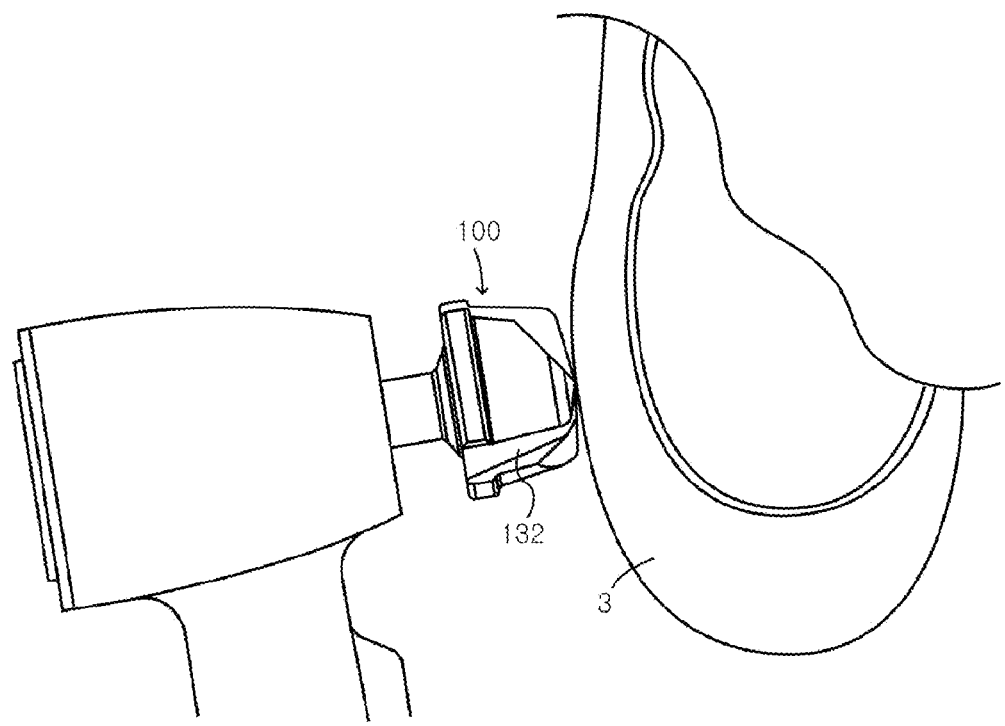
FIGS. 9a to 9c are exemplary views illustrating the figures before, during and after drilling of bones by the drill bit of the present invention.
Figure 9B:
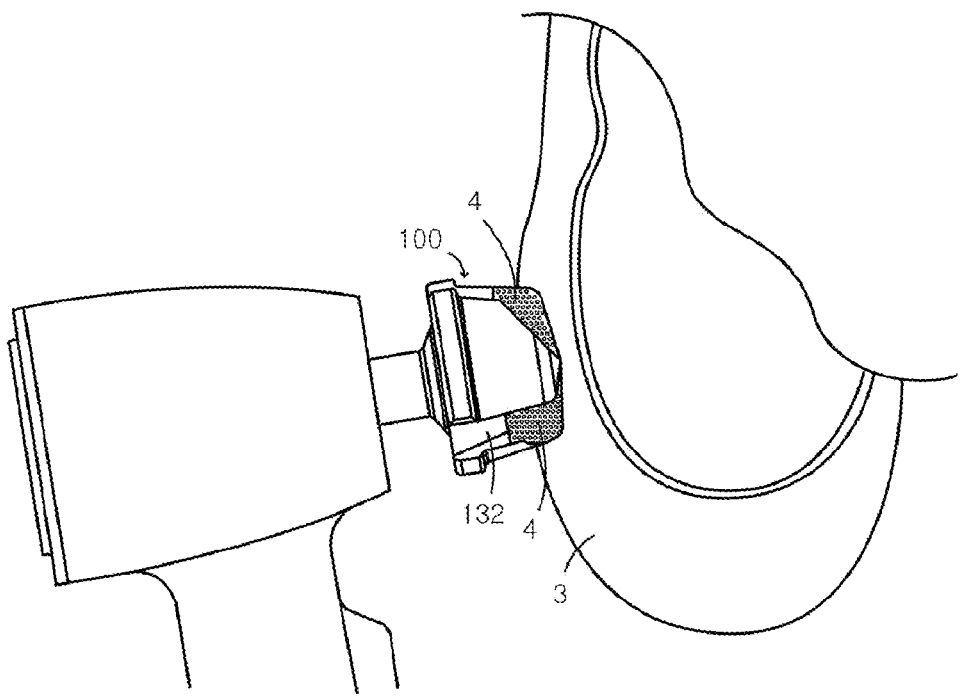
Figure 9C:
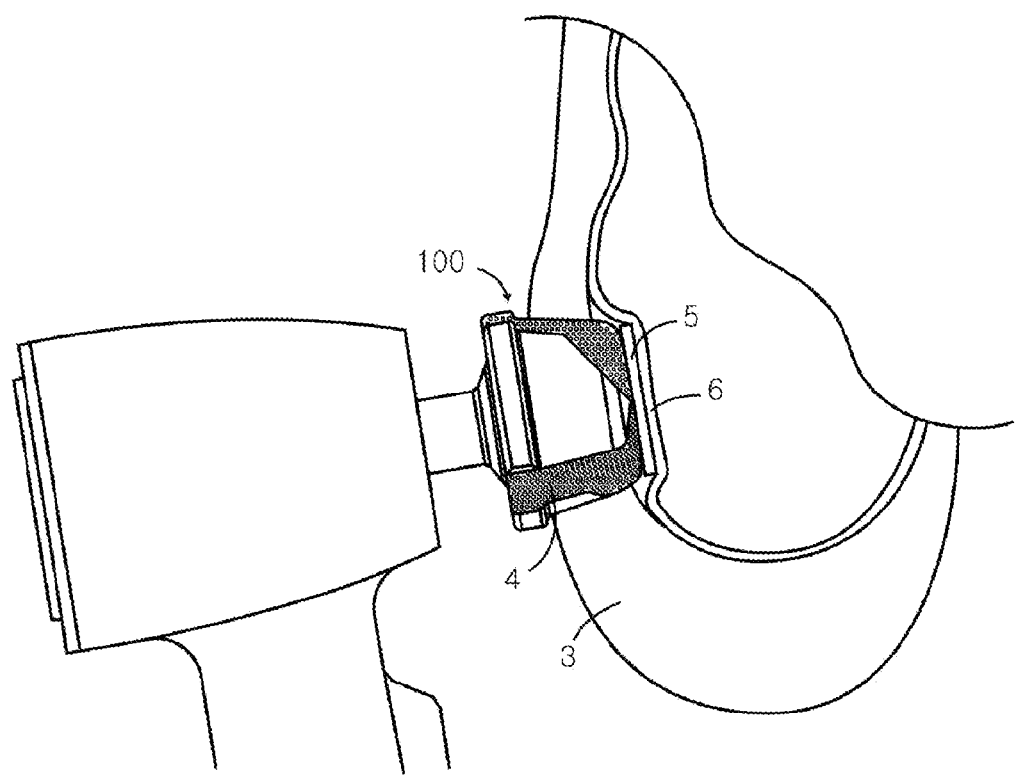

FIGS. 9a to 9c are exemplary views illustrating the figures before, during and after drilling of bones by the drill bit of the present invention.

As shown in FIG. 9a, the channels 132 of the drill bit 100 are empty before the bones 3 are drill by the drill bit 100.

As shown in FIG. 9b, when the bones 3 begin to be drilled by the drill bit 100, the channels 132 begin to be filled with the bone chips 4 cut by the drill bit 100, and the agglomerated bone chips 4 are obtained in the channels 132 when the bones are sufficiently drilled. This agglomerated bone chips 4 will be backwardly retreated from the channels 132 by the proceeding force of the drill bit 100 when they meet uncut bones.

As shown in FIG. 9c, when drill bit 100 is close to the inner wall of the bones 3, the proceeding force of the drill bit 100 is greater than the resisting force of the inner wall and then the bones become to be broken in a disk type alike to the section of the drill bit 100 before cut. And, the agglomerated bone chips 4 in the channels 132 are located before the merging point 134. Therefore, membranes 6 in the bones 3 meet the cut disk typed bone 5 or the bone chips 4 agglomerated in the channels 132, and then the membranes 6 are never damaged by the drill bit 100.

Although one embodiment of the present invention has been shown and described, the present invention is not limited to the described embodiment. Instead, it would be appreciated by those skilled in the art that changes may be made to this embodiment without departing from the principles and spirit of the invention, the scope of which is defined by the claims and their equivalents.

What is claimed is:

1. A surgical drill bit comprising a working portion for cutting a hole in a bone, and a mounting portion configured to mount to a drill or hand-piece and having a diameter or thickness smaller than that of the working portion, wherein the working portion includes:
   a body portion including a distal end surface, and a side surface of generally cylindrical or at least partially tapering shape;
   a blocking portion formed at a proximal end of the body portion and having an enlarged diameter greater than the body portion and enabling to block further approach of the surgical drill bit into the bone as the blocking portion is stopped by the bone; and
   a plurality of channels, each channel formed in a longitudinal direction of the working portion and extending from the distal end surface of the body portion, to the side surface of the body portion, and through the blocking portion,
   wherein each of said plurality of channels defines, at the body portion, a cutting blade portion configured to cut the bone upon rotation of the drill bit, and a trailing edge portion formed on an opposite side of the channel from the cutting blade portion, and the channel is configured to temporarily store bone chips therein, and then to discharge the bone chips outside from the channel,
   wherein each of the plurality of cutting blade portions have an end cutting blade, a cutting corner, and a side cutting edge that is extended toward the blocking portion,
   wherein the end cutting blades are configured to cut the surface of the bone, and they have a tilt angle of 7-9° with respect to a line perpendicular to a central axis of the body portion,
   wherein the side cutting edges are configured to cut a side wall of the hole in the bone, and they have an outward tilt angle of 7-9° with respect to the central axis of the body portion,
   wherein each of the plurality of trailing edge portions have a trailing end edge area, a trailing corner area, and a trailing side edge area that is extended toward the blocking portion,
   wherein the trailing end edge areas have a tilt angle of 20-40° with respect to the line perpendicular to the central axis of the body portion,
   wherein the trailing side edge areas have an inward tilt angle of 15-25° with respect to the central axis of the body portion.

2. The drill bit of claim 1, wherein the mounting portion is formed unitarily with the working portion.

3. The drill bit of claim 1, wherein the plurality of cutting blade portions and the plurality of channels are three, respectively, and they are formed to have equal interval of 120° with respect to the central axis of the body portion.

4. The drill bit of claim 1, wherein the plurality of cutting blade portions meet at one merging point on the central axis of the body portion.

5. The drill bit of claim 4, wherein the merging point has a steeper tilt angle than a tilt angle of the plurality of cutting blade portions defined at the distal end surface of the body portion.

6. The drill bit of claim 1, wherein a height of the end cutting blades in a direction of the central axis is 0.2-0.5 mm.

7. The drill bit of claim 1, wherein a height of the side cutting edges in a direction of the central axis is 1.0-5.0 mm.

8. The drill bit of claim 1, wherein the cutting corners are roundly formed to have a radius of curvature of 0.4-0.6 mm.

9. The drill bit of claim 1, wherein a height of the cutting corners in a direction of the central axis is 0.2-0.7 mm.

10. The drill bit of claim 1, wherein the plurality of channels have a tilt angle of 7-9° with respect to the central axis of the body portion.

11. The drill bit of claim 1, wherein the plurality of channels consist of main channels having a tilt angle of 7-9° with respect to the central axis of the body portion, and subsidiary channels having a tilt angle of 15-25° with respect to the central axis of the body portion.

12. The drill bit of claim 1, wherein a surface defined by the end cutting blades and the trailing end edge areas consists of a cutting surface and a relief surface that are substantially perpendicular to the side surface.

13. The drill bit of claim 12, wherein a juncture between the cutting surface and the side surface has a radius of curvature of 0.3-0.5 mm.

14. The drill bit of claim 12, wherein the cutting surface is near to the end cutting blades and the relief surface is near to the trailing end edge areas.

15. The drill bit of claim 12, wherein the cutting surface is formed near to the end cutting blade, and has a tilt angle of 8-12° with respect to a line perpendicular to the central axis of the body portion.

16. A drill comprising the drill bit as set forth in claim 1.

17. A surgical drill bit comprising a working portion for cutting a hole in a bone, and a mounting portion configured to mount to a drill or hand-piece and having a diameter or thickness smaller than that of the working portion, wherein the working portion includes:

a body portion including a distal end surface, and a side surface of generally cylindrical or at least partially tapering shape;

a blocking portion formed at a proximal end of the body portion and having an enlarged diameter greater than the body portion and enabling to block further approach of the surgical drill bit into the bone as the blocking portion is stopped by the bone; and a plurality of channels, each channel formed in a longitudinal direction of the working portion and extending from the distal end surface of the body portion, to the side surface of the body portion, and through the blocking portion, wherein each of said plurality of channels defines, at the body portion, a cutting blade portion configured to cut the bone upon rotation of the drill bit, and a trailing edge portion formed on an opposite side of the channel from the cutting blade portion, and the channel is configured to temporarily store bone chips therein, and then to discharge the bone chips outside from the channel, wherein each of the plurality of cutting blade portions have an end cutting blade, a cutting corner, and a side cutting edge that is extended toward the blocking portion, wherein a height of the end cutting blade in a direction of a central axis of the body portion is 0.2-0.5 mm, a height of the cutting corner in the direction of the central axis is 0.2-0.7 mm, and a height of the side cutting edge in the direction of the central axis is 1.0-5.0 mm, wherein an entire height of the body portion, that is the sum of the height of the end cutting blade, the height of the cutting corner, and the height of the side cutting edge, is less than a maximum diameter at a root area of the body portion.

18. The drill bit of claim 17, wherein the end cutting blades are configured to cut the surface of the bone, and they have a tilt angle of 7-9° with respect to a line perpendicular to the central axis of the body portion, wherein the side cutting edges are configured to cut a side wall of the hole in the bone, and they have an outward tilt angle of 7-9° with respect to the central axis of the body portion, wherein each of the plurality of trailing edge portions have a trailing end edge area, a trailing corner area, and a trailing side edge area that is extended toward the blocking portion, wherein the trailing end edge areas have a tilt angle of 20-40° with respect to the line perpendicular to the central axis of the body portion, wherein the trailing side edge areas have an inward tilt angle of 15-25° with respect to the central axis of the body portion.

* * * * *